United States Patent [19]
Lednicer

[11] 3,947,520
[45] Mar. 30, 1976

[54] COMPOUNDS AND PROCESS FOR PREPARING THE SAME

[75] Inventor: Daniel Lednicer, Kalamazoo, Mich.

[73] Assignee: The Upjohn Company, Kalamazoo, Mich.

[22] Filed: Dec. 5, 1974

[21] Appl. No.: 529,750

Related U.S. Application Data

[60] Division of Ser. No. 89,063, Nov. 12, 1970, Pat. No. 3,875,242, which is a continuation-in-part of Ser. No. 694,859, Jan. 2, 1968, abandoned, which is a continuation-in-part of Ser. No. 364,288, May 1, 1964, abandoned.

[52] U.S. Cl. ............................................. 260/590 D
[51] Int. Cl.$^2$ ........................................ C07C 49/82
[58] Field of Search ................. 260/590, 591, 590 D

[56] References Cited
UNITED STATES PATENTS 3,415,837    12/1968    Bencye et al. ..................... 260/590

*Primary Examiner*—Bernard Helfin
*Assistant Examiner*—James H. Reamer
*Attorney, Agent, or Firm*—Willard L. Cheesman; John T. Reynolds

[57] ABSTRACT

Cis and trans isomers of 1,2-diphenyl-1,2,3,4-tetrahydronaphthalenes, novel processes for the preparation thereof, and novel intermediates are disclosed herein. The novel 1,2-diphenyl-1,2,3,4-tetrahydronaphthalenes have utility as antifertility estrogenic, antiestrogenic, anti-spermatogenic, cholesterol lowering and lipid normalizing agents.

3 Claims, No Drawings

COMPOUNDS AND PROCESS FOR PREPARING THE SAME

CROSS REFERENCE TO RELATED APPLICATIONS

This is a division of application Ser. No. 89,063 now U.S. Pat. No. 3,875,242, filed Nov. 12, 1970, which is in turn a continuation-in-part application of application Ser. No. 694,859, filed Jan. 2, 1968, now abandoned which is in turn a continuation-in-part application of application Ser. No. 364,288, now abandoned filed May 1, 1964. In Ser. No. 364,288, 6-alkoxy-1,2-diphenyl-1,2,3,4-tetrahydronaphthalenes, derivatives thereof, and processes for preparing the same were disclosed. Although no stereochemistry was discussed in Ser. No. 364,288, it has now been established that the compounds disclosed therein were cis-isomers of 6-alkoxy-1,2-diphenyl-1,2,3,4-tetrahydronaphthalene and its derivatives.

BRIEF SUMMARY OF THE INVENTION

The novel 1,2-diphenyl-1,2,3,4-tetrahydronaphthalenes of this ivention, which includes both the cis- and trans-isomers have the formula:

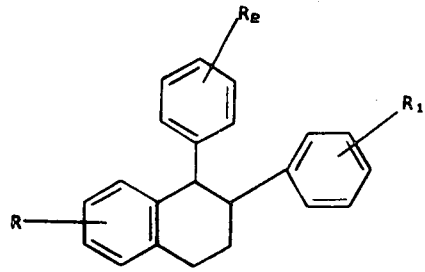

I wherein R represents alkoxy or cycloalkoxy; $R_1$ is selected from the class consisting of hydrogen, alkyl and halogen; and $R_2$ is selected from the group consisting of hydrogen, halogen, alkyl, alkoxy, alkoxy substituted by a group selected from the class consisting of (a) dihydroxyalkyl having from 2 to 5 carbon atoms, inclusive, (b) 2-amino-1-hydroxyethyl, (c) 5-(2-thioxooxazolidinyl)-, (d) 5-(2-oxooxazolidinyl)-, and (e) epoxyethyl, and the radical $-O-C_nH_{2n}-R_3$ wherein n is an integer from 1 to 6, inclusive, and $R_3$ is selected from the group consisting of carboxy and carboalkoxy.

The term "alkyl" means an alkyl radical of from 1 to 4 carbon atoms, inclusive, such as methyl, ethyl, propyl, butyl and isomeric forms thereof. The term "halogen" means fluorine, chlorine, bromine and iodine. The term "alkoxy" means alkoxy containing from 1 to 4 carbon atoms, inclusive, such as methoxy, ethoxy, propoxy, butoxy and isomeric forms thereof. The term "cycloalkoxy" means cycloalkoxy containing from 3 to 6 carbon atoms, inclusive, such as cyclopropoxy, cyclobutoxy, cyclopentyloxy, and the like. The term "dihydroxyalkyl having from 2 to 5 carbon atoms" includes 1,2-dihydroxyethyl, 1,3-dihydroxypropyl, 2,3-dihydroxypropyl, 1,4-dihydroxybutyl, and the like. The term "carbalkoxy" means the group —COOAlkyl wherein Alkyl is alkyl as hereinbefore defined.

The novel processes for making the novel compounds wherein $R_2$ is alkoxy or substituted alkoxy are illustrated in the following equations:

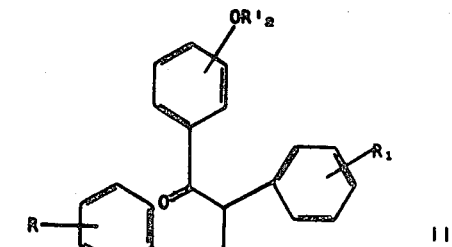

II

↓ A

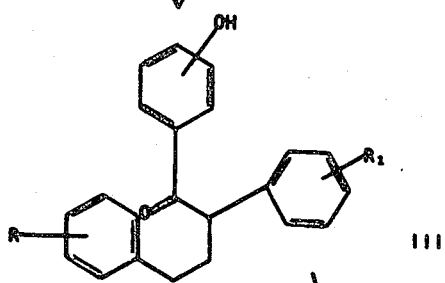

III

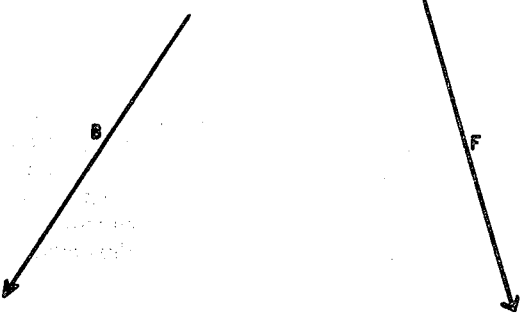

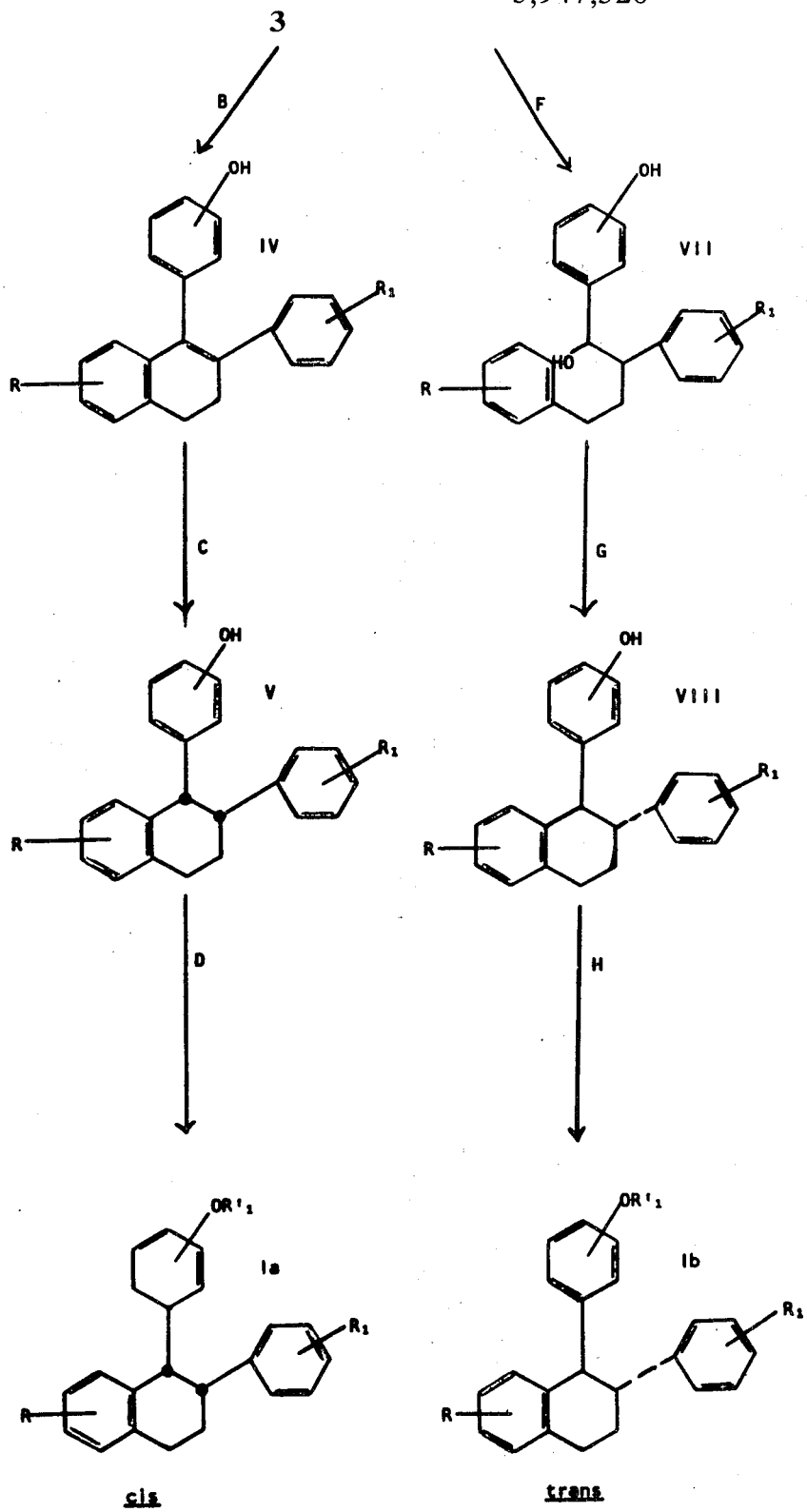

wherein R and $R_1$ are the same as above, $R'_1$ is alkyl, alkyl substituted by a group selected from the class consisting of (a) dihydroxyalkyl, having from 2 to 5 carbon atoms, inclusive, (b) 2-amino-1-hydroxyethyl-, (c) 5-(2-thioxooxazolidinyl)-, (d) 5-(2-oxooxazolidinyl)-, and (e) epoxyethyl, and the radical —$C_nH_{2n}$—$R_3$ wherein n is an integer from 1 to 6, inclusive, and $R_3$ is selected from the group consisting of carboxy and carbalkoxy.

The novel process for making the compounds of Fomula I, wherein $R_2$ is other than substituted alkoxy is illustrated in the following equations:

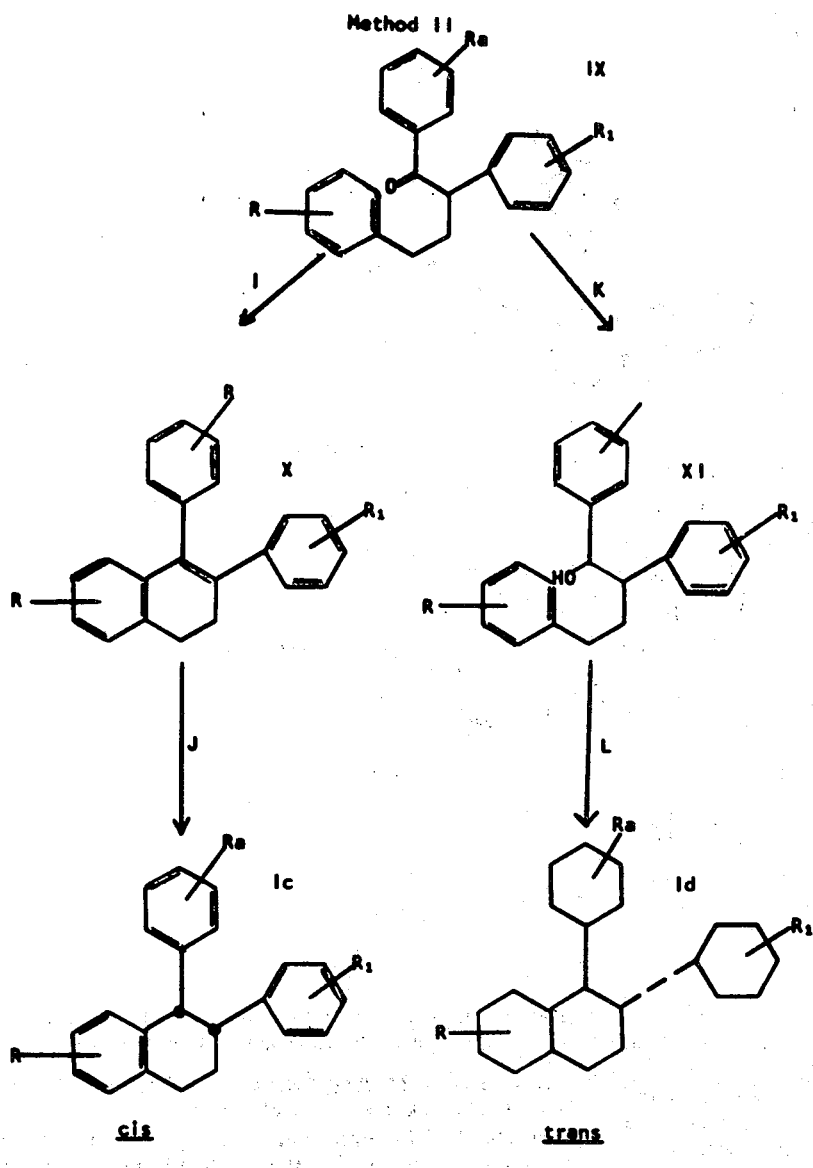

wherein R and $R_1$ are the same as above, and $R_a$ is selected from the group consisting of hydrogen, halogen, alkyl, hydroxy, and alkoxy.

DETAILED DESCRIPTION

The novel compounds of the invention are prepared in accordance with the reactions shown in the flow sheets above.

The starting phenyl substituted 1-butanones, Formulae II and IX can be prepared by (a) formylating the appropriate substituted phenyl benzyl ketone (XII), (b) subjecting the product (XIII) of the formylation to a modified Wittig reaction to form a β-hydroxy-α-phenylacrylophenone and (c) catalytically reducing the β-hydroxy-α-phenylacrylophenone. These steps are illustrated in the following equations:

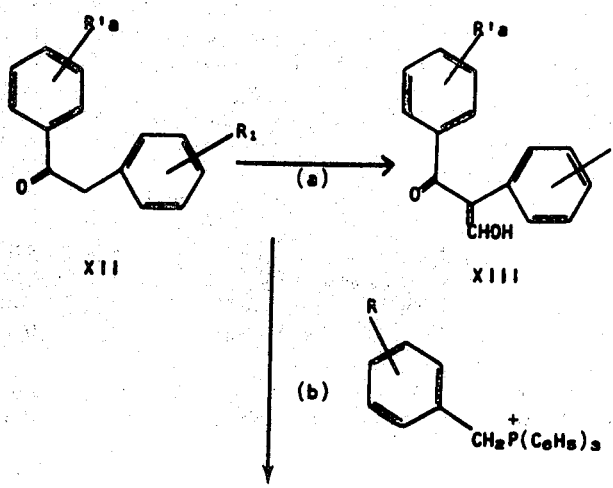

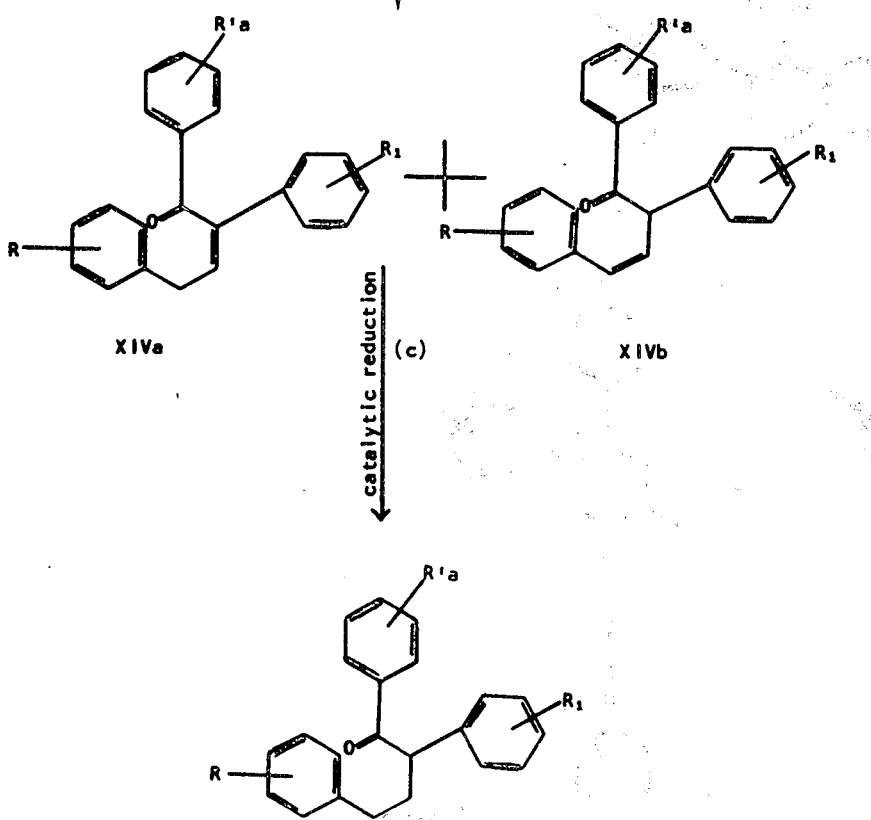

wherein R and $R_1$ are the same as above and R'a is selected from the group consisting of hydrogen, alkyl, alkoxy and halogen.

The formylation step is accomplished by treating the ketone (XII) with ethyl formate in the presence of a metal alkoxide. The starting materials for the formylation reaction are available from commercial sources. The reaction readily takes place at 25° C. however, higher or lower temperatures, e.g. 0° to 70° C. may be used, if desired.

The second step (b) is a modification of the Wittig reaction. In the basic Wittig reaction, the usual procedure involves reacting an ylide with an aldehyde. However, it has been found that high concentrations of the ylide, $(C_6H_5)_3P=CHAr$, adversely affect the reaction. For this reason, instead of using the ylide, the solid triphenyl phosphonium salt is added to a mixture of the anion of the keto-aldehyde. While a wide range of temperatures may be used in the reaction, it is preferably conducted under reflux conditions. Also, this reaction is preferably conducted in the presence of solvent such as tetrahydrofuran.

The final step (c) involves the catalytic reduction of the mixture of isomeric olefins (XIVa and XIVb) formed in step (b). It is performed by contacting the isomeric mixture with hydrogen in the presence of a noble metal catalyst. For example, hydrogen may be bubbled thru a warm solution of the isomers in the presence of a palladium catalyst.

The cis-isomers of the compound of Formula I, wherein $R_2$ is alkoxy or substituted alkoxy group, is prepared in accordance with reaction scheme A, B, C, and D set forth in the flow sheet of Method I above.

In step A, of Method I the alkylated ketone of Formula II is dealkylated to yield the hydroxy ketone of Formula III. This preferential dealkylation is readily accomplished by heating the alkylated ketone with at least 3 equivalents of aluminum chloride in benzene. The amount of aluminum chloride used is critical. It has been found that when less than 3 equivalents are used, the reaction does not proceed. Prolonged heating should be avoided in this step because it results in a reduced yield. It is preferred to conduct the reaction under reflux conditions, although higher or lower temperatures may be used, if desired.

In step B, the hydroxy ketone of Formula III is cyclized to yield the dihydronaphthalenes of Formula IV. This ring closure is effected with a solution consisting of a Lewis acid and a solvent such as benzene or toluene. The term "Lewis acid" is well known in the art and is defined succinctly by Fieser and Fieser, "Organic Chemistry", third edition, page 138 (Reinhold, 1956). Examples of such compounds are hydrogen fluoride, boron trifluoride, aresenic trifluoride, phosphorous pentafluoride, toluene sulfonic acid, titanium tetrafluoride, concentrated sulfuric acid, polyphosphoric acid, and the like. Toluene sulfonic acid is the preferred acid because of the mildness of the reaction when it is used.

The tetrahydronaphthalenes (I) are prepared by reducing the dihydronaphthalenes of Formula IV as is illustrated in step D. The reaction can be effected by contact with hydrogen in the presence of a noble metal catalyst or by using a reducing agent such as lithium in the presence of an alkanol, for example, methanol, ethanol, propanol, isobutyl alcohol or tertiary butyl alcohol and the like, and liquid ammonia. When lithium in the presence of liquid ammonia is used as the reducing agent, the reduction can be carried out by adding an approximately stoichiometric amount of lithium advantageously in the form of lithium wire, to a solution of the dihydronaphthalene (IV) in a mixture of liquid ammonia, an alcohol such as ethanol, methanol, isobutyl alcohol, tertiary butyl alcohol, and an inert organic solvent such as tetrahydrofuran, benzene, or toluene. The reduction occurs rapidly and is usually substantially complete in a period of from about 15 minutes to about 1 hour, though longer reaction periods may be necessary with certain compounds. The desired product (V) is isolated from the reaction mixture by conventional procedures; for example, by evaporation of the solvent after addition of ammonium chloride, followed by solvent extraction of the residue, evaporation of solvent from the extract, and purification of the resulting product by recrystallization or chromatography.

The tetrahydronaphthalenes (V) can be readily converted to the ethers of Formula Ia by methods well known in the art for the etherification of phenols. Illustratively, the compounds of Formula Ia wherein $R'_1$ is alkyl can be prepared by treating the compounds of Formula V with the appropriate alkyl halide in the presence of a base such as sodium hydroxide, sodium methoxide, and the like. The etherification is conducted advantageously in the presence of an inert organic solvent such as tetrahydrofuran, dioxane, a lower alkanol, for example, methanol, ethanol, and isopropyl alcohol.

Using the same procedure as above but replacing the alkyl halide with the appropriate tertiaryaminoalkylhalide

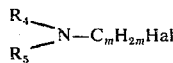

wherein Hal is halogen and $R_4$ and $R_5$ individually are similar or different alkyl groups and when taken together with the attached nitrogen atoms from the residue of a saturated heterocyclic amine containing from 5 to 7 members, inclusive, in the ring, compounds of Formula Ia wherein $R'_1$ is a tertiaryaminoalkyl group can be prepared.

The carboxyalkyl and carbalkoxyalkyl ether compounds of Formula (Ia) wherein $R'_1$ is $-C_nH_{2n}-R_3$ (wherein $R_3$ and $C_nH_{2n}$ are as hereinbefore defined) can be prepared by reaction of the appropriate hallo ester, Hal $-C_nH_{2n}-R_3$ (wherein Hal is halogen, preferably chlorine or bromine, and $-C_nH_{2n}R_3$ as hereinbefore defined) with an alkali-metal salt, preferably sodium or potassium salt, of the corresponding phenol (V). The reaction is carried out in the presence of an inert organic solvent such as tetrahydrofuran, dimethylformamide, benzene, toluene, xylene, and the like, using conditions conventional in the art for such alkylations. The carbalkoxyalkyl ether so obtained can be hydrolyzed to the corresponding free acid using conditions known in the art for hydroxylis of carboxylic acid esters, for example, by treatment with aqueous or alcoholic alkali-metal hydroxides.

Similarly the compounds of Formula (Ia) wherein $R'_1$ is an alkyl group substituted by dihydroxyalkyl as hereinbefore defined, or by epoxyethyl, can be prepared by alkylating the corresponding compounds of Formula (V) with the appropriate dihydroxyalkyl halide or epoxyalkyl halide in the presence of a base such as sodium hydroxide, sodium methoxide, and the like. The alkylation is conducted advantageously in the presence of an inert organic solvent such as tetrahydrofuran, dioxane, a loweralkanol, for example, methanol, ethanol, isopropyl alcohol, and the like.

The compounds so obtained wherein $R'_1$ represents alkyl substituted by epoxyethyl can be reacted with succinimide in the presence of a base such as pyridine, piperidine, and the like to yield the corresponding 2-succinimide-1-hydroxyethyl-substituted alkoxy compound. The latter compound is subjected to alkaline hydrolysis, for example, using aqueous or alcoholic sodium or potassium hydroxide, to yield the corresponding compound of Formula (Ia) wherein $R'_1$ is alkyl substituted by 2-amino-1-hydroxyethyl.

The latter compound is converted to the corresponding compound of Formula (Ia) wherein $R'_1$ is 5-(2-thioxooxazolidinyl)-by reaction with carbon disulfide in the presence of a base such as potassium hydroxide, sodium hydroxide, potassium carbonate, and the like. The procedures employed can be those described in the art; see, for example Bruson et al., J. Amer. Chem. Soc. 59, 2011, 1937. The reaction is preferably conducted in the presence of an inert organic solvent such as tetrahydrofuran, dioxane, ethanol, isopropyl alcohol, and the like. Elevated temperatures, e.g., the reflux temperature of the reaction mixture, are advantageously employed in the condensation.

Similarly, the compounds of Formula (Ia) wherein $R'_1$ represents alkyl substituted by 5-(2-oxooxazolidinyl)- are prepared from the corresponding compounds wherein $R_2$ represents alkyl substituted by 2-amino-1-hydroxyethyl by reacting the latter compounds with ethyl chloroformate, phosgene, or a dialkyl carbonate, in the presence of a base using procedures known in the art; see, for example, U.S. Pat. No. 2,399,188.

The method for preparing trans-isomers of the compound of Formula Ib, wherein $R'_1$ is a substituted alkyl group, is illustrated by reaction scheme A, F, G, and H in the flow sheet above. Step A has been described above.

In reaction F, the ketone of Formula (III) is reduced to yield the alcohol of Formula VII. This reduction is accomplished by reacting the ketone with lithium aluminum hydride in the presence of a solvent. The reaction proceeds readily at room temperature, but higher or lower temperatures may be used, if desired. The preferred solvent is tetrahydrofuran; however, other solvents such as benzene, toluene, or the like, may be used. The ketone of Formula III has two asymmetric centers. Hence, it was surprising that the reduction yielded only a single diasteroisomer, While the exact reason for this phenomena is not known, it is probable that the steric bulk of the groups on the carbon atom adjacent to the ketone group favor one mode of attack by the hydride. Reaction G is a cyclization and reaction H is an alkylation. They are conducted in substantially the same manner as reactions B and E, respectively.

The cis-isomers of the compound of Formula Ic, wherein $R_2$ is other than a substituted alkoxy group, are prepared by Method II illustrated by reaction scheme I and J in the flow sheet above. Step I is a cyclization reaction and step J is a reduction reaction. They are performed in substantially the same manner as the cyclization and reduction of reactions B and C, respectively, of Method 1.

The method for preparing the trans-isomers of the compound of Formula I$d$, wherein $R_2$ is a group other than a substituted alkoxy, is illustrated in reaction schemes K and L. In reaction K, the ketone of Formula IX is subjected to a reduction to yield the carbinol of Formula XI. The carbinol is then cyclized to yield the compound of Formula I$d$. The ketone reduction and the cyclization reaction are conducted in substantially the same manner as reactions F and G, respectively.

The novel compounds of the invention possess pharmacological activity. Thus, they are active an anti-fertility, estrogenic, anti-estrogenic, anti-spermatogenic, hypocholesteremic, and lipid-mobilizing agents. For example, both the trans- and cis-isomers of 1-(p-[2,3-dihydroxypropoxy]phenyl-2-phenyl-6-methoxy-1,2,3,4-tetrahydronaphthalene exhibit oral anti-fertility activity in rats when tested by the method described by Duncan et al, Proc. Soc. Exp. Biol. Med. 112, 439–442, 1963.

The novel compounds of the invention are valuable for animal pest control. For example, the compounds of the invention are formulated in combination with baits and/or attractants and placed in feeding stations accessible to undesirable rodents and other small animals including Canedae such as coyotes, foxes, wolves, jackals, and wild dogs and birds such as starlings, gulls, redwing blackbirds, pigeons, and the like, thus reducing hazards to aviation by their presence on runways and in the vicinity of airfields, the spread of disease, and destruction to property in both rural and urban areas.

For purposes of administration to birds and to mammals, including animals of economic value such as horses, cattle, sheep, pigs, mice, rats, rabbits, and the like, the novel compounds of the invention can be combined with solid or liquid pharmaceutical carriers and formulated in the form of tablets, powder packets, capsules, and like solid dosage forms, using starch and like excipients, or dissolved or suspended in suitable solvents or vehicles, for oral or parenteral administration.

The following examples are set forth to illustrate my invention and to enable persons skilled in the art to better understand and practice the invention and are not intended to limit the same.

In Example 1, a method for preparing a representative 1-(hydroxyphenyl)-4-(methoxyphenyl)-2-phenyl-1-butanone is described. These butanones are valuable compounds because they may be utilized to prepare both the cis- and trans-isomers of the corresponding 1-alkoxyphenyl- and 1-(substituted alkoxyphenyl)-2-phenyl-1,2,3,4-tetrahydronaphthalenes.

In Examples 2 and 3, methods for preparing representative cis- and trans-isomers, respectively, of substituted 1-(hydroxyphenyl)- 2-phenyl-1,2,3,4-tetrahydronaphthalenes from the corresponding 1-butanones are described.

Examples 4 to 12 describe processes for preparing representative (substituted alkoxyphenyl)-2-phenyl-1,2,3,4-tetrahydronaphthalenes from the corresponding 1-(hydroxyphenyl)-2-phenyl-1,2,3,4-tetrahydronaphthalenes. The processes used to convert both the cis- and trans-isomers of the hydroxyphenyl tetrahydronaphthalenes to their corresponding substituted alkoxyphenyl-tetrahydronaphthalenes are substantially the same.

Example 13 describes a process form aking representative 1-butanones that may be used to make substituted 1,2-diphenyl-1,2,3,4-tetrahydronaphthalenes that have substituents other than substituted alkoxy attached to the 1-phenyl radical.

Examples 14 and 15 illustrate the preparation of representative substituted cis- and trans-isomers of 1,2-diphenyl-1,2,3,4-tetrahydronaphthalenes wherein the 1-phenyl radical is substituted by a substituent other than substituted alkoxy.

EXAMPLE 1

4-(m-methoxyphenyl)-1-(p-hydroxyphenyl-1-butanone

A. m-Methoxybenzyl chloride

To an ice cooled well stirred solution of 50 g. of m-methoxybenzyl alcohol in 500 ml. of benzene there are added, over the period of 20 minutes, 29 ml. of thionyl chloride in 40 ml. of benzene. At the end of an additional 30 minutes the ice bath was removed and the solution allowed to stand for 2 hours. Following this, the mixture was heated at reflux until the evolution of gas has ceased (30 minutes). The solvent was then removed in vacuum and the product distilled at 1.5 mm. There was obtained 39.94 g. of m-methoxybenzyl chloride, b.p. 63°–69° C. A considerable residue of higher boiling tar remained.

The corresponding o-methoxybenzyl chloride and p-methoxybenzyl chloride are obtained by employing o-methoxybenzyl alcohol and p-methoxybenzyl alcohol, respectively, in place of m-methoxybenzyl alcohol in the above procedure.

B. m-Methoxybenzyltriphenylphosphonium chloride

A mixture composed of 44.16 g. of m-methoxybenzyl chloride and 74.0 g. of triphenyl phosphine was heated in an oil bath at 100° C. for 1 hour. The resulting solid cake was broken up and recrystallized from a methylene chloride:acetonitrile solution.

There was obtained 86.1 g. of m-methoxybenzyl-triphenyl-phosphonium chloride, m.p. 271°–272° C. The mother liquors were concentrated and allowed to cool. An additional 21.6 g. of product, m.p. 271°–272° C. was obtained. Total yield = 91%.

Analysis. Calcd. for $C_{26}H_{14}ClOP$: C, 74.53; H, 5.77; Cl, 8.47. Found: C, 74.56; H, 6.01; Cl. 8.56.

Similarly, the para- and ortho-methoxybenzyltriphenyl-phosphonium chlorides are obtained by reacting the appropriate methoxybenzyl chloride with triphenyl-phosphine.

C. p-Methoxy-β-hydroxy-α-phenylacrylophenone

A stirred solution of 2.3 g. of sodium in 30 ml. of ethanol was cooled in an ice:methanol bath. There was then added 8.25 ml. of ethyl formate. The stirring was stopped and the mixture allowed to stand in the cold for 2 hours. The stirring was then resumed and 22.6 g. of finely powdered anisyl benzyl ketone was added. Following 16 hours stirring first in the cold and then at room temperature, the mixture was diluted with ice-water to make 350 ml. The precipitated solid was collected on a filter and washed well with ice-water to afford 9.33 g. of recovered anisyl benzyl ketone, m.p. 61°–66° C.

13

The filtrate was acidified in the cold to afford 14.40 g. of p-methoxy-β-hydroxy-α-phenylacrylophenone, m.p. 82°–86° C; yield, 96% (based on ketone consumed).

The analytical sample, m.p. 83.5°–86.5° C. was obtained by recrystallization from Skellysolve B hexanes.

Analysis. Calcd. for $C_{16}H_{14}O_3$: C, 75.57; H, 5.55. Found: C, 74.95 75.09; H, 5.53, 4.98.

The corresponding ortho- and meta-isomers are obtained by employing the appropriate ortho- and meta-methoxy ketones in place of anisyl benzyl ketone in the procedure of step C.

D. Mixture of isomeric 4-(m-methoxyphenyl)-1-(p-methoxyphenyl)-2-phenyl-1-butenones To a well-stirred, ice cooled solution of 10.32 g. of p-methoxy-β-hydroxy-α-phenylacrylophenone in 430 ml. of tetrahydrofuran there was added 1.84 g. of sodium hydride (56% in mineral oil). Following 40 minutes stirring, 17.9 g. of finely powdered m-methoxybenzyltriphenylphosphonium chloride was added. Following 18 hours heating at reflux, the bulk of the solvent was removed in vacuum. The residue was dissolved in ether and water. The organic layer was separated and washed in turn with water and a saturated solution of sodium chloride. The ethereal solution was taken to dryness and placed on 2 l. of magnesium silicate (Florisil). The mineral oil was washed off with Skellysolve B hexanes. Elution with 10% acetone afforded 13.76 g. of the isomeric 4-(m-methoxyphenyl-1-(p-methoxyphenyl)-2-phenyl-1-butenones as a series of gums (yield, 84%).

Similarly, other substituted 1,2,4-triphenyl-1-butenones are obtained by reacting the appropriate triphenylphosphonium chloride with the appropriate β-hydroxy-α-phenylacrylophenone using the procedure described in step D.

E. 4-(m-Methoxyphenyl)-1-(p-methoxyphenyl)-2-phenyl-1-butanone

A solution of the crude isomeric 4-(m-methoxyphenyl)-1-(m-methoxyphenyl-2-phenyl-1-butenones obtained from step D (13.76 g.) in 200 ml. of ethnaol was shaken under hydrogen with 1.40 g. of 10% palladium on charcoal (starting at 50 p.s.i.). When 1 molar equivalent of hydrogen was taken up, (10 min.) the rate of gas uptake slowed considerably. The reaction was stopped and the catalyst removed by filtration. The slightly oily solid which remained when the filtrate was taken to dryness was recrystallized from methanol, there was obtained 10.78 g. (79%) of 4-(m-methoxyphenyl)-1-(p-methoxyphenyl-2-phenyl-1butanone, m.p. 79°–85° C.

The analytical sample from a previous run melted at 81°–84° C.

Analysis. Calcd. for $C_{24}H_{24}O_3$: C, 79.97; H, 6.71. Found: C, 79.66; H, 6.81.

Using the above procedure, other 1,2,4-triphenyl-1-butanones are obtained by replacing the isomeric mixture of 4-(m-methoxyphenyl)-1-(p-methoxyphenyl)-2-phenyl-1-butenones with a mixture of the appropriate-1-butenones.

F. 1-(p-Hydroxyphenyl)-4-(m-methoxyphenyl)-2-phenyl-1-butanone

A mixture of 11.65 g. of 4-(m-methoxyphenyl-1-(p-methoxyphenyl)-2-phenyl-1-butanone and 13.6 g. of aluminum chloride in 270 ml. of benzene was heated at reflux for 3½ hours. The solution was allowed to cool and washed in turn with 2.5 N hydroxhloric acid, water and a saturated solution of sodium chloride. The organic layer was then extracted with 5 portions of 110 ml. each of N sodium hydroxide. Acidification of this last extract gave 11.04 g. of the crude phenol. A single recrystallization from aqueous methanol afforded 8.42 g. of 1(p-hydroxyphenyl)-4-(m-methoxyphenyl)-2-phenyl-1-butanone, m.p. 125°–129° C. (yield, 75%)

Analysis. Calcd. for $C_{23}H_{22}O_3$: C, 79.74; H, 6.40. Found: C, 79.38; H, 6.87.

Similarly, other derivatives of 1-(hydroxyphenyl)-2-phenyl-4-phenyl-1-butanone are obtained by dealkylating the appropriate 1-methoxyphenyl-2-phenyl-4-phenyl-1-butanone using the procedure described in step F.

EXAMPLE 2 cis-1-(p-Hydroxyphenyl-6-methoxy-2-phenyl-1,2,3,4-tetrahydronaphthalene

A.

1-(p-Hydroxyphenyl)-6-methoxy-2-phenyl-3,4-dihydronaphthalene

A solution of 5.70 g. of 1-(p-hydroxyphenyl)-4-(m-methoxyphenyl)-2-phenyl-1-butanone and 5.70 g. of p-toluenesulfonic acid in 250 ml. of benzene was heated under a Dean-Starke trap until the evolution of water ceased (2½ hours). The mixture was allowed to cool, diluted with water and washed in turn with aqueous sodium bicarbonate, water and a saturated solution of sodium chloride. The residue which remained when the organic layer was taken to dryness was recrystalized from acetone:cyclohexane. There was obtained 4.37 g. (82%) of 1-(p-hydroxyphenyl)-6-methoxy-2-phenyl-3,4-dihydronaphthalene, m.p. 158°–162° C.

B.

cis-1-(p-Hydroxyphenyl)-6-methoxy-2-phenyl-1,2,3,4-tetrahydronaphthalene

A solution of 1 g. of 1-(p-hydroxyphenyl-6-methoxy-2-phenyl-3,4-dihydronaphthalene in 20 ml. of tetrahydrofuran and 1 ml. of tertiarybutyl alcohol was added to 100 ml. of ammonia redistilled from lithium. To this there was added 42 mg. of lithium wire; the color faded very quickly. After 5 to 10 minutes an additional 42 mg. of lithium were added. The blue color this time prevailed for 20 minutes. After the addition of 1 g. of solid ammonium chloride, the mixture was taken to dryness under a stream of nitrogen. The gummy solid which remained was suspended in water and the suspension was acidified with acetic acid. The solid was collected on a filter and recrystallized twice from methanol to yield 0.40 g. of cis-1-(p-hydroxyphenyl)-6-methoxy-2-phenyl-1,2,3,4-tetrahydronaphthalene, having a melting point of 188°–190° C.

Analysis. Calcd. for $C_{23}H_{22}O$: C, 83.60; H, 6.71. Found: C, 83.45; H, 6.89.

Other cis-1-(hydroxyphenyl)-2-phenyl-1,2,3,4-tetrahydronaphthalene derivatives are obtained by replacing 1-(p-hydroxyphenyl)-4-(m-methoxyphenyl)-2-phenyl-1-butanone with the appropriately substituted 1-(hydroxyphenyl)-2-phenyl-4-phenyl-1-butanones in the procedures of Example 2. Representative of the tetrahydronaphthalenes prepared are:

6-ethoxy-1-(p-hydroxyphenyl)-2-phenyl-,
1-(o-hydroxyphenyl)-2-phenyl-7-ethoxy-, 1-(p-hydroxyphenyl)-2-phenyl-6-propoxy-,
1-(o-hydroxyphenyl)-2-phenyl-6-propoxy-,
6-butoxy-1-(p-hydroxyphenyl)-2-phenyl-,
6-butoxy 1-(o-hydroxyphenyl)-2-phenyl-,
2-(p-chlorophenyl)-1-(p-hydroxyphenyl)-6-methoxy-,
2-(p-chlorophenyl)-6-cyclopropoxy-1-(p-hydroxyphenyl)-,
2-(o-chlorophenyl)-1-p-hydroxyphenyl-6-methoxy-,
2-(m-chlorophenyl)-1-(p-hydroxyphenyl)-6-methoxy-,
2-(p-chlorophenyl)-1-(o-hydroxyphenyl)-6-methoxy-,
2-(p-chlorophenyl)-1-(p-hydroxyphenyl)-5-methoxy-,
2-(p-chlorophenyl)-1-(p-hydroxyphenyl)-7-methoxy-,
2-(p-chlorophenyl)-1-(p-hydroxyphenyl)-8-methoxy-,
2-(p-bromophenyl)-1-(p-hydroxyphenyl)-6-methoxy-,
1-(p-hydroxyphenyl)-6-methoxy-2-(p-tolyl)-,
2-(p-fluorophenyl)-1-(p-hydroxyphenyl-1,2,3,4-tetrahydronaphthalenes.

The cis-1-(hydroxyphenyl)-1,2,3,4-tetrahydronaphthalenes so obtained and the corresponding trans-isomers are converted to the derivatives of the corrresponding cis- and trans-isomers of the 1-(dihydroxyalkoxyphenyl),1-(carbalkoxyalkoxyphenyl)-, 1-(carboxyalkoxyphenyl)-, 1-(epoxyalkoxyphenyl)-, 1-[(2-amino-1-hydroxyethyl)alkoxyphenyl]-, 1-{[5-(2-thiooxooxazolidinyl)]-alkoxyphenyl}-, 1-{[5-(2-oxooxazolidinyl)]alkoxyphenyl}-, and 1-(alkoxyphenyl)-2-phenyl-1,2,3,4-tetrahydronaphthalene using the procedures set forth in Examples 4 through 12.

EXAMPLE 3 trans-1-(p-Hydroxyphenyl)-6-methoxy-2-phenyl-1,2,3,4-tetrahydronaphthalene (Method 1)

A.
1-(p-Hydroxyphenyl)-4-(m-methoxyphenyl)-2-phenyl-1-butanol

A solution of 2.0 g. of 1-(p-hydroxyphenyl)-4-(m-methoxyphenyl)-2-phenyl-1-butanone in 50 ml. of teterahydrofuran was added to 1.0 g. of lithium aluminum hydride in 10 ml. of tetrahydrofuran over a period of 10 minutes. Following 2 hours stirring at room temperature, the mixture was cooled in ice and 50 ml. each of saturated aqueous ammonium chloride and water were added. The inorganic gel was removed by filtration through Super Cel (infusorial earth). The organic layer was diluted with ether, washed with water and a saturated solution of sodium chloride and taken to dryness. The residual solid was recrystallized twice from benzene to give 0.01 g. of 1-(p-hydroxyphenyl)-4-(m-methoxyphenyl)-2-phenyl-1-butanol, melting point 100°–103° C.

Analysis. Calcd. for $C_{23}H_{24}O_3$: C, 79.28; H, 6.94. Found: C, 79.38; H, 6.93.

B.
trans-1-(p-Hydroxyphenyl)-6-methoxy-2-phenyl-1,2,3,4-tetrahydronaphthalene A solution of 6.35 g. of 1-(p-hydroxyphenyl)-4-(m-methoxyphenyl)-2-phenyl-1-butanone (step A) and 3.80 g. of p-toluenesulfonic acid in 250 ml. of benzene was heated for 2 hours under a Dean-Starke Trap. The solution was then allowed to cool and washed in turn with aqueous sodium bicarbonate and brine. The solution was taken to dryness and the residue chromatographed over silica gel (elution with methylene chloride). Those fractions which were similar by thin layer chromatography analysis were combined and chromatographed over Florisil (elution with 5% acetone). Those fractions which crystallized on trituration with ether were combined and recrystallized twice from ether. There was obtained 3.32 g. of trans-1-(p-hydroxyphenyl)-6-methoxy-2-phenyl-1,2,3,4-tetrahydronaphthalene as its ether solvate, melting point 55°–57.5° C. NMR:doublet (1H) 4.05δ (J=10 cps).

Analysis. Calcd. for $C_{23}H_{22}O_2 \cdot (C_2H_5)_2O$: C, 80.16; H, 7.97. Found: C, 80.32; H, 8.17.

Similarly, trans-isomers corresponding to the cis-1-hydroxyphenyl-2-phenyl-1,2,3,4-tetrahydronaphthalenes listed in Example 2 are obtained by employing the appropriate trans-1-(hydroxyphenyl)-2-phenyl-4-phenyl-1-butanone in place of cis-1-(p-hydroxyphenyl)-4-(m-methoxyphenyl)-2-phenyl-1-butanone in the procedure of Example 3.

EXAMPLE 4 cis-1-[p-(2,3-Dihydroxypropoxy)phenyl]-6-methoxy-2-phenyl-1,2,3,4-tetrahydronaphthalene To a solution of 551.5 g. of cis-1-(p-hydroxyphenyl)-6-methoxy-2-phenyl-1,2,3,4-tetrahydronaphthalene (Example 2) in 9,350 ml. of methanol there was added 393 ml. of 4.65 N sodium methoxide solution all at once. The mixture was stirred until solution was complete. Then 196.3 g. of 1-chloro-2,3-propanediol was added all at once and the solution was heated under reflux for 18 hours after which the mixture was distilled under reduced pressure to dryness. The residue was dissolved in 35 l. of an ether-water mixture. The ether layer was evaporated, washed with 8 l. of water, washed with 8 l. of a saturated sodium chloride solution and then dried over anhydrous sodium sulfate. The dried ether mixture was filtered and distilled. The crude residue was chromatographed over Florisil (elution with first 10% then 50% acetone in Skellysolve B hexanes). The fractions obtained from the chromatography were evaporated to dryness to yield a crude product. The crude solid was dissolved in ether, gravity filtered and concentrated. This concentrate was cooled overnight at 5° to 10° C., vacuum filtered, and dried in a vacuum oven at 50° C. to obtain a crystalline solid product, melting point 125°–129° C. The filtrate was concentrated to obtain a 2nd crop of product, melting point 126°–129° C. The combined product was dissolved in warm ether, concentrated and then mixed with Skellysolve B hexanes while the ether was at the boiling point. Shortly thereafter, crystallization started and the mixture was cooled with stirring and chilled overnight. The mixture was then filtered and dried in a vacuum oven at 50° C. to constant weight to obtain cis-1-[p-[2,3-dihydroxypropoxy)-phenyl] -6-methoxy-2-phenyl-1,2,3,4-tetrahydronaphthylene, melting point 125.3°–134.8° C.

Analysis. Calcd. for $C_{26}H_{28}O_4$: C, 77.20; H, 6.98; O, 15.82. Found: C, 77.43; H, 6.89; O, 15.92.

Using the above procedure but replacing 1-chloro-2,3-propanediol by 1-chloro-2,3-butanediol and 5-bromo-1,3-pentanediol, there are obtained cis-1-[p-(2,3-dihydroxybutoxy)phenyl]- and cis-1-(p-(3,5-dihydroxypentyloxy)phenyl]-6-methoxy-2-phenyl-1,2,3,4-tetrahydropthalene, respectively.

EXAMPLE 5 trans-1-]p-(2,3-Dihydroxypropoxy]phenyl)-6-methoxy-2-phenyl-1,2,3,4-tetrahydronaphthalene To a solution of 2.0 g. of trans-1-(p-hydroxyphenyl)-6-methoxy-2-phenyl-1,2,3,4-tetrahydronaphthylene (Example 3) in 40 ml. of methanol there was added 1.5 ml. of 4.65 N methanolic sodium methoxide followed after 10 minutes by 0.73 g. of 1-chloro-2,3-propanediol. Following 18 hours heating under reflux the mixture was taken to dryness. The residue was dissolved in ether, methylene chloride and water. The organic layer was separated, washed with water and a saturated solution of sodium chloride and taken to dryness. This residue was chromatographed on Florisil. Elution with 8% acetone gave 0.41 g. of recovered starting phenol. Elution with 50% acetone gave the product as a series of amorphous gums. Each of these showed a single spot on thin layer chromatography. These were combined to give a gum which resisted attempts at crystallization. A solution of the gum in benzene was frozen in Dry-ice acetone and freeze dried to give trans-1-[p-(2,3-dihydroxypropoxy]phenyl]-6-methoxy-2-phenyl-1,2,3,4-tetrahydronaphthalene as an amorphous powder.

Analysis. Calcd. for $C_{26}H_{28}O_4$: C, 77.20; H, 6.98. Found: C, 76.24; H, 7.19.

EXAMPLE 6 cis-Ethyl-2-[p-(6-methoxy-2-phenyl-1,2,3,4-tetrahydro-1-naphthyl)phenoxy]-2-methylpropionate To a solution of 2.5 g. of cis-1-(p-hydroxyphenyl)-6-methoxy-2-phenyl-1,2,3,4-tetrahydronaphthalene in 13 ml. of dimethylformamide and 65 ml. of benzene, is added with stirring 0.35 g. of sodium hydride as a 53% suspension in mineral oil. When the effervescence has subsided the solution is treated with a solution of 1.5 g. of ethyl 2-bromo-2-methylpropionate in 15 ml. of benzene and the mixture is heated under reflux for 17 hours. The resulting mixture is allowed to cool, washed with water and with a saturated sodium chloride solution, and the organic layer is evaporated to dryness. The residue is chromatographed on a column of magnesium silicate (Florisil) and the column is eluted with hexanes containing increasing proportions of acetone. Those fractions which, on the basis of infrared absorption analysis are found to contain the desired product, are combined and evaporated to dryness. The residue is recrystallized from petroleum ether to yield cis-ethyl 2-]p-(6-methoxy-2-phenyl-1,2,3,4-tetrahydro-1-naphthyl)phenoxy]-2-methylpropionate in the form of a crystalline solid.

Similarly, using the above procedure but replacing ethyl 2-bromo-2-methylpropionate by ethyl bromoacetate, ethyl 5-bromovalerate and methyl 9-bromocaprate, there are obtained cis-ethyl p-(6-methoxy-2-phenyl-1,2,3,4-tetrahydro-1-naphthyl) phenoxyacetate, cis-ethyl 5-[p-(6-methoxy-2-phenyl-1,2,3,4-tetrahydro-1-naphthyl)phenoxy]valerate and cis-methyl 9-[p-(6-methoxy-2-phenyl-1,2,3,4-tetrahydro-1-naphthyl)-phenoxy]caprate, respectively.

Also, using the above procedure but replacing cis-1-(p-hydroxyphenyl)-6-methoxy-2-phenyl-1,2,3,4-tetrahydronaphthylene with trans-1-(p-hydroxyphenyl)-6-methoxy-2-phenyl-1,2,3,4-tetrahydronaphthalene there are obtained the corresponding trans-compound.

EXAMPLE 7 cis-2-[p-(6-methoxy-2-phenyl-1,2,3,4-tetrahydro-1-naphthyl)phenoxy]-2-methylpropionic acid A solution of 1.42 g. of cis-ethyl 2-[p-(6-methoxy-2-phenyl-1,2,3,4-tetrahydro-1-naphthyl)phenoxy]-2-methylpropionate (Example 6) and 3 ml. of 50% aqueous potassium hydroxide in 50 ml. of methanol is heated under reflux for 5 hours. The reaction mixture is then evaporated to dryness and the residue is suspended in water and made strongly acid by the addition of 2.5 N hydrochloric acid. The solid which separates is isolated by filtration and recrystallized twice from aqueous methanol. There is thus obtained cis-2-[p-(6-methoxy-2-phenyl-1,2,3,4-tetrahydro-1-naphthyl)-phenoxy]-2-methylpropionic acid in the form of a crystalline solid.

Using the same procedure, cis-p-(6-methoxy-2-phenyl-1,2,3,4-tetrahydro-1-naphthyl)phenoxyacetic acid, cis-5-[p-(6-methoxy-2-phenyl-1,2,3,4-tetrahydro-1-naphthyl)phenoxy]valeric acid, and cis-9-[p-(6-methoxy-2-phenyl-1,2,3,4-tetrahydro-1-naphthyl)-phenoxy]capric acid, respectively, are obtained from the corresponding ethyl and methyl esters (prepared as described in Example 6).

Similarly, the corresponding trans acids are obtained by utilizing the above procedure, but replacing the cis-hydroxy compound with the corresponding trans-hydroxy compound.

EXAMPLE 8 cis-1-[p-(2,3-Epoxypropoxy)phenyl]-6-methoxy-2-phenyl-1,2,3,4-tetrahydronaphthalene Using the procedure described in Example 6, but replacing ethyl 2-bromo-2-methylpropionate by epichlorohydrin, there is obtained cis-1-[p-(2,3-epoxypropoxy)phenyl]-6-methoxy-2-phenyl-1,2,3,4-tetrahydronaphthalene.

Similarly, using the procedure of Example 6, but replacing ethyl 2-bromo-2-methylpropionate by 3-bromo-1,2-epoxybutane (Chemical Abstracts 36, 404, 1942) and 5-bromo-1,2-epoxy-pentane (Wilson, J. Chem. Soc. 1945, 48), there are obtained cis-1[p-(2,3-epoxy-1-methylpropoxy)phenyl]- and cis-1-[p-(4,5-epoxy-pentyloxy)phenyl]-6-methoxy-2-phenyl-1,2,3,4-tetrahydronaphthylene, respectively.

The corresponding trans compounds can be prepared according to the above procedure by replacing the cis-hydroxy compound with the corresponding trans hydroxy compound.

EXAMPLE 9 cis-1-[p-(3-Amino-2-hydroxypropoxy)phenyl]-6-methoxy-2-phenyl-1,2,3,4-tetrahydronaphthalene and the hydrochloride thereof A mixture of 3.0 g. of cis-1-[p-(2,3-epoxypropoxy)-phenyl]-6-methoxy-2-phenyl-1,2,3,4-tetrahydronaphthalene, 0.80 g. of succinimide and 4 drops of piperidine in 100 ml. of absolute ethanol is heated under reflux for 17 hours. The resulting mixture is concentrated to approximately one-third volume by distillation under reduced pressure and the residue is diluted with water. The mixture so obtained is extracted with methylene chloride and the methylene chloride extract is washed with water and saturated sodium chloride solution before being evaporated to dryness. The residue is recrystallized from aqueous alcohol to yield cis-1-[p-(3-succinimido-2-hydroxy-propoxy)phenyl]-6-methoxy-2-phenyl-1,2,3,4-tetrahydronaphthalene. The latter compound is then heated under reflux for 20 hours with a solution of 16 g. of sodium hydroxide in 320 ml. of ethanol. The resulting product is concentrated by distillation under reduced pressure and the residue is extracted with a mixture of methylene chloride and water. The methylene chloride solution is separated, washed with water, and taken to dryness. Hydrogen chloride is bubbled through a solution of the residue in ether. The solid which separates is isolated by filtration, and dried. There is thus obtained cis-1-[p-(3-amino-2-hydroxy-propoxy)phenyl]-6-methoxy-2-phenyl-1,2,3,4-tetrahydronaphthalene hydrochloride. The corresponding free base is obtained by dissolving the hydrochloride in methylene chloride, washing the resulting solution with an aqueous sodium bicarbonate solution, and evaporating the methylene chloride solution to dryness.

Using the above procedure, but replacing cis-1-[p-(2,3-epoxypropoxy)phenyl]-6-methoxy-2-phenyl-1,2,3,4-tetrahydronaphthalene by cis-1-[p-2,3-epoxy-1-methylpropoxy)phenyl]- and cis-1-[p-(4,5-epoxypentyloxy)phenyl]-6-methoxy-2-phenyl-1,2,3,4-tetrahydronaphthalene, there are obtained cis-1-[p-(3-amino-2-hydroxy-1-methylpropoxy)phenyl]- and cis-1-[p-(5-amino-4-hydroxypentyloxy)phenyl]-6-methoxy-2-phenyl-1,2,3,4-tetrahydronaphthalene, respectively, and the hydrochlorides thereof.

Using the above procedure, but replacing the cis-2,3-epoxypropoxy compounds with trans-2,3-epoxypropoxy compounds, there are obtained the corresponding trans-amino-hydroxyalkoxy compounds.

EXAMPLE 10 cis-5-{[p-(6-Methoxy-2-phenyl-1,2,3,4-tetrahydro-1-naphthyl)phenoxy]methyl}-2-oxazolidinethione A solution of 2.8 g. of cis-1-[p-(3-amino-2-hydroxypropoxy) phenyl]-6-methoxy-2-phenyl-1,2,3,4-tetrahydronaphthalene in 100 ml. of ethanol is mixed with 0,85 ml. of carbon disulfide and 3.1 ml. of 25% aqueous potassium hydroxide solution. The resulting mixture is heated under reflux for 4 hours and then concentrated under reduced pressure. The concentrate is suspended in water and the suspension acidified with 2.5 N hydrochloric acid. The suspension is extracted with hot methylene chloride and the methylene chloride extract is evaporated to dryness. There is thus obtained cis-5-{[p-(6-methoxy-2-phenyl-1,2,3,4-tetrahydro-1-naphthyl)phenoxy]methyl}-2-oxazolidinethione.

Using the above procedure but replacing cis-1-[p-(3-amino-2-hydroxypropoxy(phenyl]-6-methoxy-2-phenyl-1,2,3,4-tetrahydronaphthalene by cis-1-[p-(2,3-epoxy-1-methylpropoxy)phenyl]- and cis-1-[p-4,5-epoxypentyloxy)phenyl]-6-methoxy-2-phenyl-1,2,3,4-tetrahydronaphthalene, there are obtained 5-{1-[p-(6-methoxy-2-phenyl-1,2,3,4-tetrahydro-1-naphthyl)-phenoxy]ethyl}- and 5-{3-[p-(6-methoxy-2-phenyl-1,2,3,4-tetrahydro-1-naphthyl)-phenoxy]propyl}-2-oxazolidinethione, respectively.

The corresponding trans compounds can be prepared in accordance with the above procedure by replacing the cis-starting material by the corresponding trans-starting material.

EXAMPLE 11 cis-5-{[p-(6-Methoxy-2-phenyl-1,2,3,4-tetrahydro-1-naphthyl)phenoxy]methyl}-2-oxazolidinone To a vigorously stirred suspension of 3.7 g. of cis-1-[p-(3-amino-2-hydroxypropoxy)phenyl]-6-methoxy-2-phenyl-1,2,3,4-tetrahydronaphthalene in 30 ml. of toluene and 30 ml. of 12.5% aqueous potassium hydroxide solution is added dropwise over a short period 3.2 g. of phosgene in 10 ml. of toluene. The mixture is then taken to dryness in vacuum and the residue dissolved in methylene chloride. The methylene chloride solution is extracted with dilute hydrochloric acid before being evaporated to dryness. There is thus obtained cis-5-{[p-(6-methoxy-2-phenyl-1,2,3,4-tetrahydro-1-naphthyl)phenoxy]methyl}-2-oxazolidinone.

Using the above procedure but replacing cis-1-[p-(3-amino-2-hydroxypropoxy)phenyl]-6-methoxy-2-phenyl-1,2,3,4-tetrahydronaphthalene by cis-1-[p-2,3-epoxy-1-methylpropoxy)phenyl]- and cis-1-[p-(4,5-epoxypentyloxy)phenyl]-6-methoxy-2-phenyl-1,2,3,4-tetrahydronaphthalene, there are obtained cis-5{1-[p-(6-methoxy-2-phenyl-1,2,3,4-tetrahydro-1-naphthyl)-phenoxy]ethyl}- and cis-5-{3-[p-(6-methoxy-2-phenyl-1,2,3,4-tetrahydro-1-naphthyl)-phenoxy]propyl}-2-oxazolidinone, respectively.

EXAMPLE 12 cis-1-(p-Methoxyphenyl)-6-methoxy-2-phenyl-1,2,3,4-tetrahydronaphthalene

Using the procedure described in Example 4, but replacing (1-chloro-2,3-propanediol) by methyl iodide and reducing the reaction time to 2 hours, there is obtained cis-1-(p-methoxyphenyl)-6-methoxy-2-phenyl-1,2,3,4-tetrahydronaphthalene.

EXAMPLE 13

1,2-Diphenyl-4-(m-methoxyphenyl)-1-butanone

A. α-Phenyl-β-hydroxyacrylophenone

Six grams of sodium was dissolved in 75 ml. of absolute ethanol (heating). The solution was cooled in ice-methanol and treated with 21.5 ml. of ethyl formate. Following 2½ hours in the cold, 50 g. of finely powdered desoxybenzoin was added with vigorous agitation. The ice was allowed to melt and the pasty mixture stirred for 16 hours at room temperature. The mixture was then diluted with ice-water to 800 ml. and the precipitated solid collected on a filter. There was thus obtained 12.81 g. of recovered desoxybenzoin. The filtrate was again cooled and cautiously acidified with concentrated hydrochloric acid. The precipitated solid was collected on a filter and dried in vacuum to afford 38.12 g. of α-phenyl-β-hydroxyacrylophenone, m.p. 110°–114° C. (lit. 110° C.). Yield (based on desoxybenzoin consumed) 90%.

B. Mixture of isomeric 1,2-diphenyl-4-(m-methoxyphenyl)-1-butenones

To an ice-cooled solution of 3.06 g. of α-phenyl-β-hydroxy-acrylophenone in 100 ml. of tetrahydrofuran there was added 0.59 g. of a 56% dispersion of sodium hydride in mineral oil. Following 30 minutes stirring 5.70 g. of finely powdered m-methoxybenzyltriphenylphosphonium chloride was added to the solution. The yellow mixture was heated at reflux for 24 hours. The bulk of the solvent was removed in vacuum and ether was added. The organic layer was washed with water and a saturated solution of sodium chloride and taken to dryness. The residue was placed on a column of 500 ml. of Florisil. This was washed with Skellysolve B hexanes (to wash off the mineral oil) and then eluted with 5% acetone in benzene. The oils which came over were combined to afford 3.76 g. of a mixture of the isomers of 1,2-diphenyl-4-(m-methoxyphenyl-1-butenone, λmax. 1700, 1690 cm. $^{-1}$.

C. 1,2-Diphenyl-4-(m-methoxyphenyl)-1-butanone

A mixture of the crude isomeric 1,2-diphenyl-4-(m-methoxyphenyl)-1-butenones obtained in step B above was dissolved in 200 ml. of ethanol with warming. There was then added 0.37 g. of 10% palladium on charcoal. The mixture was shaken under hydrogen until 1 mole was absorbed (5 minutes). The catalyst was removed by filtration and the filtrate taken to dryness. The residual gum, λ max. 1700 cm. $^{-1}$, is predominately a single material, as is shown by thin layer chromatography analysis.

Using the above procedure, other 1,2-diphenyl-4-phenyl-1-butanones are obtained by replacing the isomeric mixture of 1,2-diphenyl-4-(m-methoxyphenyl)-1-butenone with the appropriate mixture of 1-butenones.

EXAMPLE 14 cis-1,2-Diphenyl-6-methoxy-1,2,3,4-tetrahydronaphthalene

A. 1,2-Diphenyl-6-methoxy-3,4-dihydronaphthalene

A solution of 3.76 g. of crude 1,2-diphenyl-4-(m-methoxyphenyl)-1-butanone and 0.75 g. of p-toluenesulfonic acid in 60 ml. of benzene was heated at reflux under a Dean-Starke trap for 2½ hours. The solution was diluted with ether and washed in turn which aqueous sodium bicarbonate, water and brine. The organic layer was taken to dryness and the residue chromatographed over 400 ml. of Florisil (elution with 0.75% acetone). The crystalline fractions were combined and recrystallized from Skellysolve B hexanes. There was obtained 1.57 g. of 1,2-diphenyl-6-methoxy-3,4-dihydronaphthalene, m.p. 98°–101° C.

B.
cis-1,2-Diphenyl-6-methoxy-1,2,3,4-tetrahydronaphthalene

A solution of 0.63 g. of 1,2-diphenyl-6-methoxy-3,4-dihydronaphthalene in 20 ml. of tetrahydrofuran and 1 ml. of tert.butyl alcohol was added to 100 ml. of ammonia redistilled from lithium. To this there was added 28 ml. of lithium wire; the color faded very quickly. After 5 to 10 minutes an additional 28 mg. of lithium were added. The blue color this time prevailed for 20 minutes. After the addition of 1 g. of solid ammonium chloride, the mixture was taken to dryness under a stream of nitrogen. The residue was then washed with ether and methylene chloride. The solid which remained when the extracts were taken to dryness was recrystallized from ethanol. There was thus obtained 0.53 g. of cis-1,2-diphenyl-6-methoxy-1,2,3,4-tetrahydronaphthalene having a melting point of 160° to 162° C.

One further crystallization from the same solvent gave an analytical sample, m.p. 166° to 168° C.

Analysis. Calcd. for $C_{23}H_{22}O$: C, 87.86; H, 7.05. Found: C, 87.30; H, 7.13.

Using the procedure described in Example 14 but replacing 1,2-diphenyl-4-(m-methoxyphenyl)-1-butanone with the appropriately substituted butanone is productive of the corresponding substituted 1,2-diphenyl-1,2,3,4-tetrahydronaphthalenes. Representative of the tetrahydronaphthalenes so prepared are:

cis-1-(p-chlorophenyl-6-methoxy-2-phenyl-,
cis-6-methoxy-1-(p-methylphenyl-2-phenyl-,
cis-1-(p-ethylphenyl)-6-methoxy-2-phenyl-,
cis-1-(p-chlorophenyl)-6-methyl-2-phenyl-,
cis-1-(p-chlorophenyl)-7-methoxy-2-phenyl-,
cis-6-methoxy-2-(p-methylphenyl)-1-phenyl-,
cis-1-(p-chlorophenyl)-2-(p-chlorophenyl)-6-methoxy-,
cis-2-(p-ethylphenyl)-6-methoxy-1-phenyl-,
cis-1-(m-chlorophenyl)-6-methoxy-2-phenyl-,
cis-2-(p-chlorophenyl)-6-methoxy-1-(p-tolyl)-,
cis-2-(o-chlorophenyl)-6-methoxy-1-(p-tolyl-,
cis-2-(m-chlorophenyl)-6-methoxy-1-(p-tolyl)-,
cis-6-cyclopropoxy-1,2-diphenyl-,
cis-1-(p-bromophenyl)-6-methoxy-2-phenyl-,
cis-2-(p-bromophenyl)-6-methoxy-1-phenyl-,
cis-2-(p-chlorophenyl)-6-methoxy-1-phenyl-,
cis-6-methoxy-1-phenyl-2-(p-tolylphenyl)-,
cis-1-(p-chlorophenyl)-2-phenyl-7-methoxy-,
cis-1-(o-chlorophenyl)-2-phenyl-8-methoxy-,
cis-2-(m-chlorophenyl)-6-methoxy-1-phenyl-1,2,3,4-tetrahydronaphthalenes.

EXAMPLE 15 trans-1,2-Diphenyl-6-methoxy-1,2,3,4-tetrahydronaphthalene

A. 1,2-diphenyl-4-(m-methoxyphenyl)-1-butanol

Using the procedure of step A of Example 3, but replacing 1-(p-hydroxyphenyl)-4-(m-methoxyphenyl-2-phenyl-1-butanone by 1,2-diphenyl-4-(m-methoxyphenyl)-1-butanone there is obtained 1,2-diphenyl-4-(m-methoxyphenyl)-1-butanol.

Similarly, by using the procedure described in step A of Example 3, but replacing 1-(p-hydroxyphenyl)-2-phenyl-4-(m-methoxyphenyl)-1-butanone by the appropriately substituted 1,2,4-triphenyl-1-butanone, the corresponding substituted 1,2,4-triphenyl-1-butanols are obtained. Representative of the 1,2,4-triphenyl-1-butanols so prepared are:

1-(p-chlorophenyl)-4-(m-methoxyphenyl)-2-phenyl-,
1-(p-chlorophenyl-4-(p-methoxyphenyl-2-phenyl-,
4-(m-methoxyphenyl)-1-(p-methyphenyl)-2-phenyl-,
2-(p-bromophenyl)-4-(m-methoxyphenyl)-1-phenyl-,
1-(p-chlorophenyl)-2-(p-chlorophenyl)-4-(m-methoxyphenyl)-,
2-(p-chlorophenyl)-4-(m-methoxyphenyl)-1-(p-tolyl-,
2-(m-chlorophenyl)-4-(m-methoxyphenyl)-1-phenyl-,
4-(m-methoxyphenyl)-2-(m-methylphenyl)-1-phenyl-1-butanols-, B.
trans-1,2-diphenyl-6-methoxy-1,2,3,5-tetrahydronaphthalene Using the procedure of step B of Example 3, but replacing 5-(p-hydroxyphenyl)-2-phenyl-4-(m-methoxyphenyl)-1-butanol by 1,2-diphenyl-4-(m-methoxyphenyl)-1-butanol there is obtained 1,2-diphenyl-6-methoxy-1,2,3,4-tetrahydronaphthalenes.

Similarly, by using the procedure of step B of Example 3, but replacing 1-(p-hydroxyphenyl)-4-(m-methoxyphenyl)-2-phenyl-1-butanol by the appropriately substituted butanol the corresponding substituted trans-1,2-tetrahydronaphthalenes are obtained. Representative of the trans tetrahydronaphthalenes so obtained are the trans-isomers corresponding to the cis-1,2-diphenyl-1,2,3,4-tetrahydronaphthalenes disclosed in Example 14.

I claim:

1. A compound having the formula:

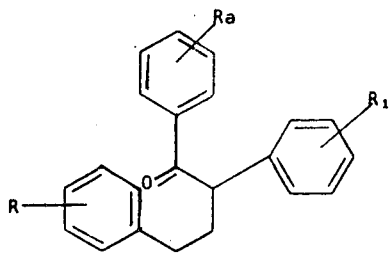

wherein R represents alkoxy or cycloalkoxy; $R_1$ is selected from the group consisting of hydrogen, lower alkyl and halogen; and Ra is selected from the class consisting of hydrogen, halogen, alkyl, hydroxy and alkoxy, wherein the alkyl and alkoxy radicals each contain from 1 to 4 carbon atoms, inclusive, and the cycloalkoxy radical contains from 3 to 6 carbon atoms, inclusive.

2. A compound of claim 1 wherein R is m-methoxy, $R_1$ is hydrogen and Ra is p-methoxy.

3. A compound of claim 1 wherein R is m-methoxy, $R_1$ is hydrogen and Ra is p-hydroxy.

* * * * *